United States Patent
Roudebush et al.

(10) Patent No.: US 9,272,061 B2
(45) Date of Patent: Mar. 1, 2016

(54) STERILIZATION TRAY FOR INSTRUMENTS

(71) Applicants: H. Richard Roudebush, Indianapolis, IN (US); Ronald C. Estes, New Palestine, IN (US)

(72) Inventors: H. Richard Roudebush, Indianapolis, IN (US); Ronald C. Estes, New Palestine, IN (US)

(73) Assignee: Estes Design and Manufacturing, Inc., Indianapolis, IN (US)

( * ) Notice: Subject to any disclaimer, the term of this patent is extended or adjusted under 35 U.S.C. 154(b) by 0 days.

(21) Appl. No.: 14/369,278

(22) PCT Filed: Feb. 7, 2013

(86) PCT No.: PCT/US2013/025197
§ 371 (c)(1),
(2) Date: Jun. 27, 2014

(87) PCT Pub. No.: WO2013/119850
PCT Pub. Date: Aug. 15, 2013

(65) Prior Publication Data
US 2015/0010440 A1    Jan. 8, 2015

Related U.S. Application Data

(60) Provisional application No. 61/595,854, filed on Feb. 7, 2012.

(51) Int. Cl.
*A61L 2/26* (2006.01)

(52) U.S. Cl.
CPC .............. *A61L 2/26* (2013.01); *A61L 2202/24* (2013.01)

(58) Field of Classification Search
CPC .............................. A61L 2/26; A61L 2202/24

USPC .......................................................... 422/300
See application file for complete search history.

(56) References Cited

U.S. PATENT DOCUMENTS

| 4,643,303 | A  | 2/1987 | Arp et al. |
| 6,012,577 | A  | 1/2000 | Lewis et al. |
| 6,713,029 | B1 | 3/2004 | Krafft et al. |
| 2004/0206711 | A1 | 10/2004 | Hoftman |
| 2011/0002811 | A1 | 1/2011 | Dane et al. |

FOREIGN PATENT DOCUMENTS

FR         2886856    * 12/2006

OTHER PUBLICATIONS

English abstract for FR 28886856, published Dec. 2006, inventor: Bertrand.*
Application No. PCT/US2013/025197, International Searching Authority, International Search Report, Apr. 15, 2013.
Application No. PCT/US2013/025197, International Searching Authority, Written Opinion of the International Searching Authority, Apr. 15, 2013.

* cited by examiner

*Primary Examiner* — Sean E Conley
(74) *Attorney, Agent, or Firm* — Ice Miller LLP

(57) ABSTRACT

The disclosure of the present application includes a sterilization tray for instruments. In an exemplary embodiment of a sterilization tray of the present disclosure, the sterilization tray comprises a sheet having a first end, an opposing second end, and a center portion between the first end and second end, in which the center portion having an undulating profile with a plurality of peaks and troughs and having a plurality of openings formed through the sheet. The openings are positioned and formed to receive one or more instruments. In at least one embodiment, the center portion includes a corrugated profile. Alternatively, the center portion includes a triangular or saw-tooth profile. In at least one embodiment, the distance between adjacent peaks of the center portion defines a wave having a length, and the center portion includes a non-uniform profile comprised of one or more waves of varying lengths.

30 Claims, 17 Drawing Sheets

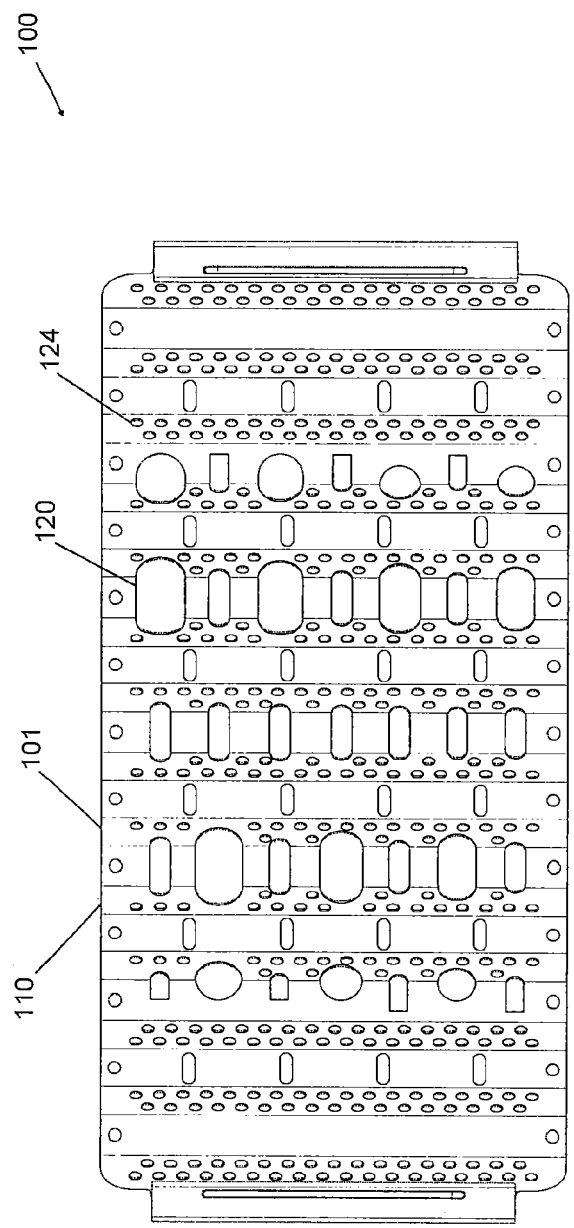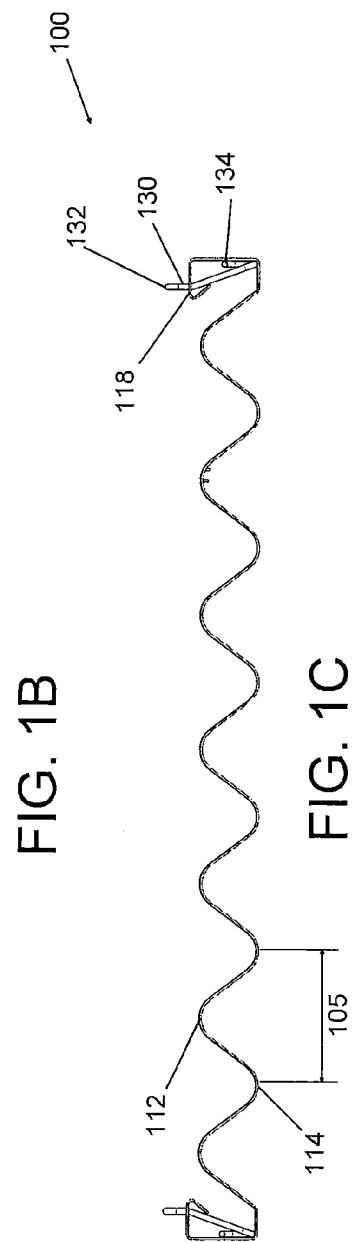

STERILIZATION TRAY FOR INSTRUMENTS

PRIORITY

The present application is related to, claims the priority benefit of, and is a United States 35 U.S.C. §371 national stage entry of, Patent Cooperation Treaty Patent Application Serial No. PCT/US2013/025197, filed Feb. 7, 2013, which is related to, and claims the priority benefit of U.S. Provisional Patent Application Ser. No. 61/595,854, filed Feb. 7, 2012. The contents of each of these applications are hereby incorporated by reference in their entirety into this disclosure.

BACKGROUND

In the field of surgical instrument sterilization, sterilization trays have traditionally been used to hold the surgical instruments for transportation and sterilization. Conventional trays have employed metal brackets riveted to a metal panel to cradle and secure each instrument in place and to keep the instruments from contacting one another during the sterilization process. Securing and separating the instruments is important for the effectiveness of the sterilization process and further helps maintain the instruments of a surgical kit in an organized and easily selectable fashion. Conventional trays utilizing multiple brackets for each individual instrument are generally very complex and require considerable time to manufacture and assemble because each type of instrument may require a unique bracket arrangement. For example, conventionally each instrument may require at least two separate brackets and four rivets. Moreover, due to the wide variety of surgical kits used in the medical industry, each type of kit requires a specialized set of brackets and other mounting hardware, which further adds to the cost and complexity of manufacturing trays for different types of surgical kits.

Some sterilization trays are manufactured using polymer-based materials. Though these trays address some of the shortcomings described, these trays are not suitable for all sterilization processes. While the medical community in the United States typically uses high-pressure saturated steam sterilization using an autoclave, other countries and regions prefer chemical sterilization. Such chemical sterilization techniques include immersion in a chemical bath of liquid sterilants or oxidizing agents such as the combination of hydrogen peroxide and peracetic acid, and aldehydes such as glutaraldehyde and, more recently, o-phthalaldehyde. The chemicals used for chemical sterilization are often not compatible with the materials used for polymer-based sterilization trays. Consequently, such trays are often not an option.

Accordingly, there is a need for a less costly, lighter weight, and more versatile sterilization tray that is compatible with both steam and chemical sterilization processes.

BRIEF SUMMARY

The disclosure of the present application includes a sterilization tray for instruments. In an exemplary embodiment of a sterilization tray of the present disclosure, the sterilization tray comprises a sheet having a first end, an opposing second end, and a center portion between the first end and second end, in which the center portion comprising an undulating profile having a plurality of peaks and troughs and having a plurality of openings formed through the sheet. The openings are positioned and configured to receive one or more instruments. The one or more instruments comprises a set of surgical instruments. In at least one embodiment, the center portion comprises a corrugated profile. Alternatively, the center comprises a saw-tooth or triangular profile. Alternatively, the distance between adjacent peaks of the center portion defines a wave having a profile and a length, and the center portion comprises a non-uniform profile comprised of one or more waves of varying lengths.

In at least one embodiment, the plurality of openings are formed such that the one or more instruments lie substantially on a plane across the peaks and troughs of the center portion. The openings are further formed such that there is clearance between each opening and each of the corresponding one or more instruments. The sheet further comprises a plurality of perforations formed through the sheet and arranged between the openings. In at least one embodiment, the first end and second end are each formed at an angle such that a plurality of trays may be stacked one upon another. The tray further comprises at least one handle. The at least one handle is formed integral with at least the first end or second end of the sheet such that it extends through and above a top surface of the first end or second end and acts as an indexing feature where multiple trays are stacked.

In at least one embodiment, the tray further comprises a support frame attached to the sheet, the support frame having at least one handle formed therein. In at least one embodiment, the sheet includes indicia imprinted on the sheet. The sheet is formed of a non-corrosive metal, such as stainless steel or aluminum. In at least one embodiment, the tray further comprises a hinged lid rotatable about the sheet and configured to be secured in a closed configuration by a latch. Alternatively, the tray comprises a cover disposed upon and removably attached to the first end and second end of the sheet, the cover capable of substantially retaining the one or more instruments.

In at least one embodiment, the disclosure includes a kit of instruments comprising a tray having a sheet having a first end, an opposing second end, and a center portion between the first end and second end, where the center portion is formed with an undulating profile having a plurality of peaks and troughs, and a plurality of openings formed through the sheet, where the openings are positioned and formed to receive one or more instruments. The kit further includes a set of instruments each positioned within the plurality of openings such that the one or more instruments lie substantially on a plane across the peaks and troughs of the center portion and a cover disposed upon and removably attached to the first end and second end, the cover capable of substantially retaining the set of instruments.

BRIEF DESCRIPTION OF THE DRAWINGS

The above mentioned embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein:

FIG. 1B shows a plan view of a sterilization tray for instruments, according to an embodiment of the present disclosure;

FIG. 1C shows a side view of a sterilization tray for instruments, according to an embodiment of the present disclosure;

Like reference numerals indicate the same or similar parts throughout the several figures.

Figure 1A:
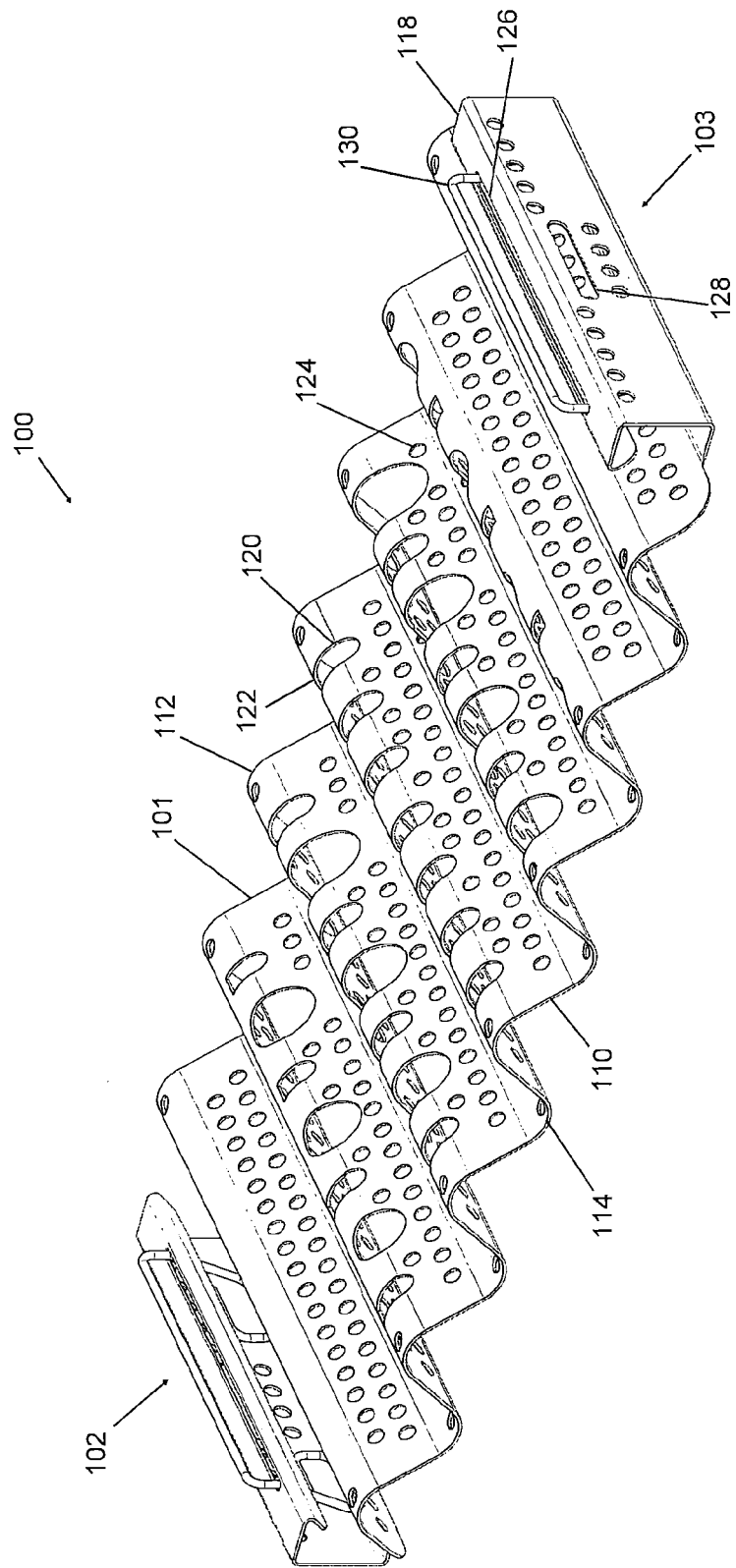
FIG. 1A shows a perspective view of a sterilization tray for instruments, according to an embodiment of the present disclosure.

An overview of the features, functions and/or configuration of the components depicted in the various figures will now be presented. It should be appreciated that not all of the features of the components of the figures are necessarily described. Some of these non-discussed features, such as various couplers, etc., as well as discussed features are inherent from the figures. Other undiscussed features may be inherent in component geometry and/or configuration.

DETAILED DESCRIPTION

The present application discloses various sterilization trays and methods for using and constructing the same. According to one aspect of the present disclosure, a sterilization tray for instruments is disclosed. For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIGS. 1A-1D depict a sterilization tray that can be used to retain instruments. As shown in FIG. 1A, a sterilization tray 100 includes a single sheet 110 having a first end 102 and a second end 103, positioned opposite one another, and a center portion 101 that joins the first and second ends 102, 103 together. As shown in FIG. 1C, the center portion 101 may be formed into a corrugated or wave-like profile (i.e., in the side view) having a plurality of peaks 112 and troughs 114 along its longitudinal axis running from the first end 102 to the second end 103. The first and second ends 102, 103 may be formed at an angle to the center portion 101 so as to extend above the peaks 112 and enable multiple trays 100 to be stacked upon one another without contacting the peaks 112 or troughs 114 of adjacent trays 100. A sub-portion of the center portion 101 extending from one peak 112 or one trough 114 to the next respective peak 112 or trough 114 defines a wave 105 of a given profile and length. As used herein, the term "profile" refers to the shape when viewed from the side.

Figure 1D:
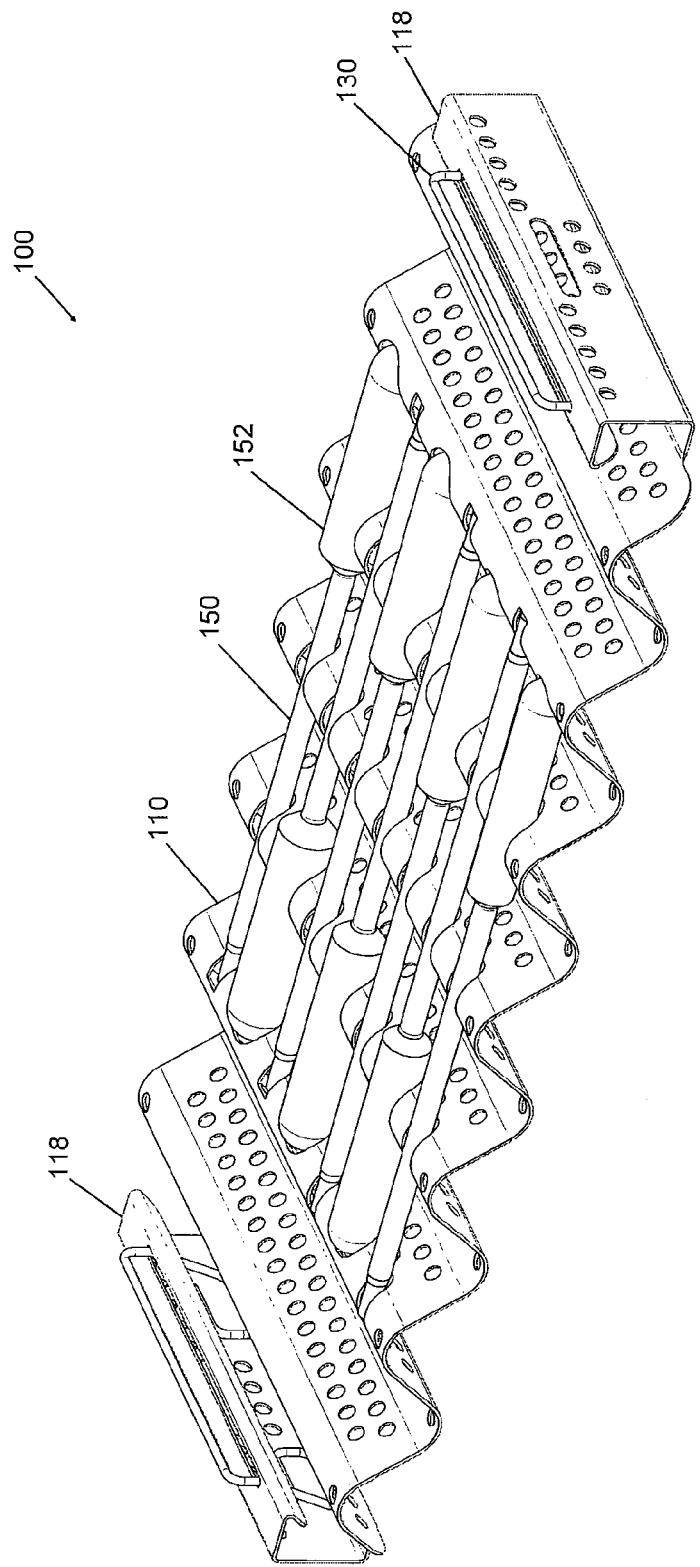
FIG. 1D shows a perspective view of a sterilization tray for instruments including an instrument set, according to an embodiment of the present disclosure.

The center portion 101 may further include a plurality of openings 120 formed through the sheet 110 defined by edges 122. As shown in FIG. 1B, the openings 120 may have various contours in plan view such that the sheet 110 is capable of both supporting and substantially retaining a plurality of surgical instruments 150 for organization, transportation, storage, handling and sterilization, as shown in FIG. 1D. Specifically, the openings 120 are formed to match the contour of each instrument 150 in a set of instruments as that contour intersects each wave 105. Accordingly, as shown in FIG. 1D, where the width of an instrument 150 in plan view is relatively large, the width of the corresponding opening 120 is relatively large and vice versa. As a result, multiple openings 120 may work in concert to support and substantially retain each individual instrument 150 at two or more locations as the instruments 150 lie across the peaks 112 and troughs 114 of the sheet 110 and at least partially in the openings 120. As used herein, the phrase "across the peaks and troughs" is intended to mean intersecting the peaks 112 and positioned above the troughs.

Moreover, because the openings 120 are formed to fit the contour of each instrument 150 of a set of instruments, each type of instrument 150 has a specific intended location on the sheet 110, whereby the edges 122 of the openings 120 coincide with corresponding shape of an instrument 150 where the instrument 150 is intended to lie across the peaks 112 and troughs 114 of the sheet 110. Consequently, the tray 100 functions to both retain and organize the instruments 150 for easy retrieval and use by a user. Further, the single sheet 110 with various openings 120 takes the place of the numerous bracket components used in conventional sterilization trays. It will be appreciated that any type and number of instruments may be retained by the tray 100, including but not limited to surgical instruments used for hip replacement, knee replacement, dental surgery, etc.

The openings 120 may be formed such that a slight clearance distance is maintained between the edges 122 of each opening 120 and the corresponding surface of each instrument 150. The slight clearance distance enables the instruments 150 to be freely placed unto and removed from the tray 100 and to enable the free flow of sterilization fluids around each instrument. For example, the opening 120 may be formed to be one-eighth inch larger than its corresponding instrument 150 at the location where the instrument 150 contacts the sheet 110. However, the clearance distance between the edges 122 of each opening 120 and the corresponding surface of each instrument 150 may be minimized to enable the tray 100 to retain all instruments 150 as the tray 100 is titled up to 45 degrees longitudinally, transversely, or on a compound angle between the longitudinal and transverse directions.

The sterilization tray 100 may be easily adapted to different instrument sets via different configurations of the plurality of openings 120 in the sheet 110. For example, an instrument set suitable for hip replacement surgery will generally be different from one appropriate for shoulder surgery, which will generally be different from one appropriate for dental surgery. Different configurations of the plurality of openings 120 may differ relative to the number, size, and contour of the openings 120. As shown in FIG. 1C, the vertical distance between the peaks 112 and the troughs 114 defines a height of the center portion 101, and the height of the center portion 101 may be selected to accommodate a given instrument set. Consequently, larger instruments 150 may generally require a center portion 101 of greater height, and smaller instruments may generally allow for a center portion 101 of lesser height. Similarly, the length of the wave 105 may also be selected to accommodate different sets of instruments, whereby relatively small instruments may be best supported by a tray 100 having a relatively small wave length and vice versa. Thus, by varying combinations of the height of the center portion 101, the length and profile of the wave 105, and the number, size, and contour of the openings 120, separate embodiments of the tray 100 can be formed to accommodate all manner of instrument sets. FIGS. 2A-2C, 3A-3B, 5, 6, 7A-7B, and 8A-8B show sterilization trays 200, 300, 500, 600, 700, and 800, respectively, each a different embodiment of the tray 100 for different types of instrument sets.

Referring to FIG. 1D, a specific configuration (i.e., height of the center portion 101, length of the wave 105, and number, size, and contour of the openings 120) of the tray 100 may be selected to support each instrument 150 of a set of instruments such that a topmost edge 152 of each instrument 150 lies on the same plane, the plane lying below a top surface 118. Consistent and uniform positioning of the instruments 150 to lie on a plane below the top surface 118 enables easy handling of multiple trays 100 simultaneously, enables trays 100 to be stacked on top of one another within an autoclave without interference, and enables an entire set of instruments 150 to be held securely in place when a cover is attached to the tray 100 as disclosed more fully herein. Further, consistent and uniform positioning of the instruments 150 on the same plane facilitates easy retrieval and use of the instruments 150 by a user.

Figure 2A:
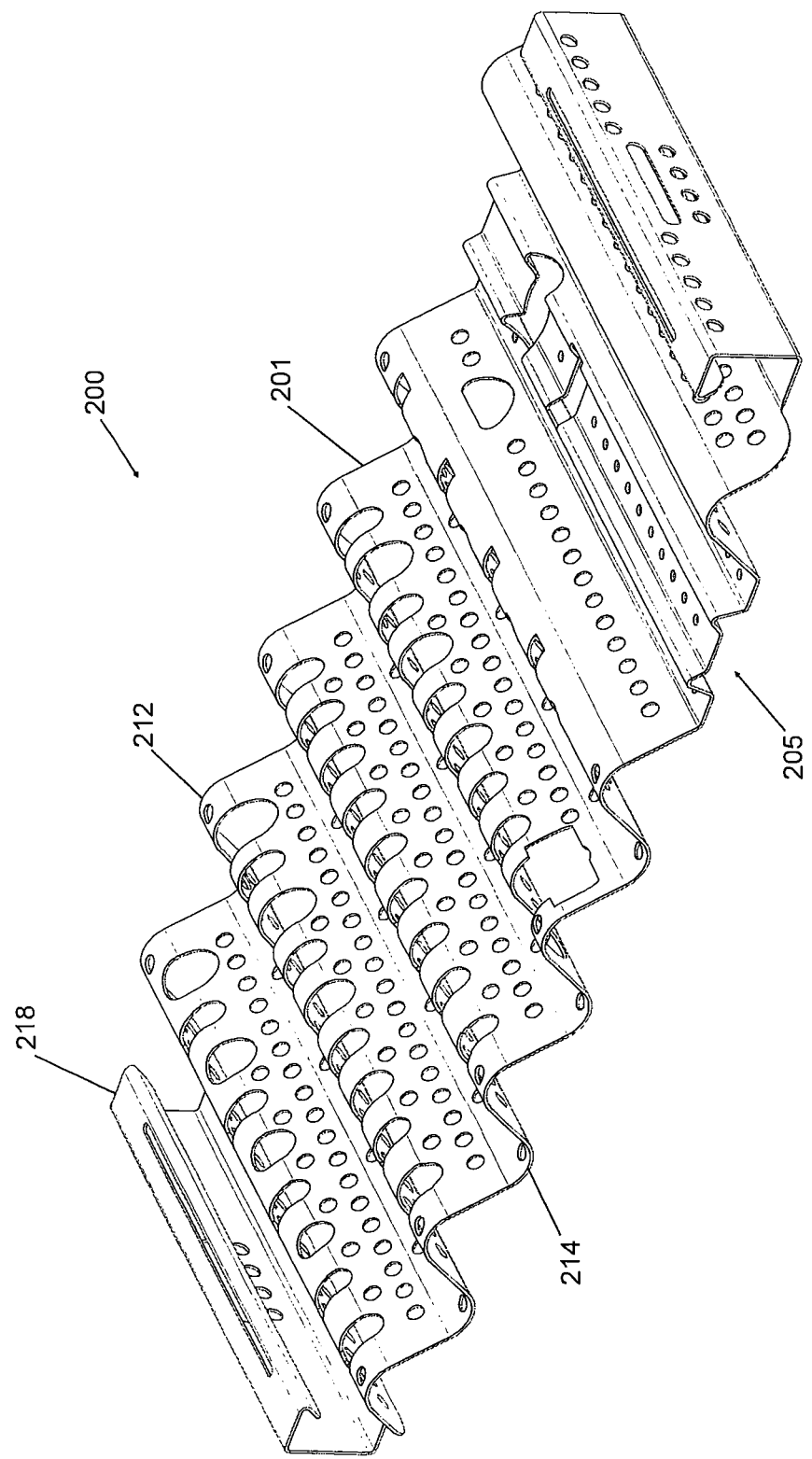
FIG. 2A shows a perspective view of a sterilization tray for instruments, according to an embodiment of the present disclosure.
Figure 2B:
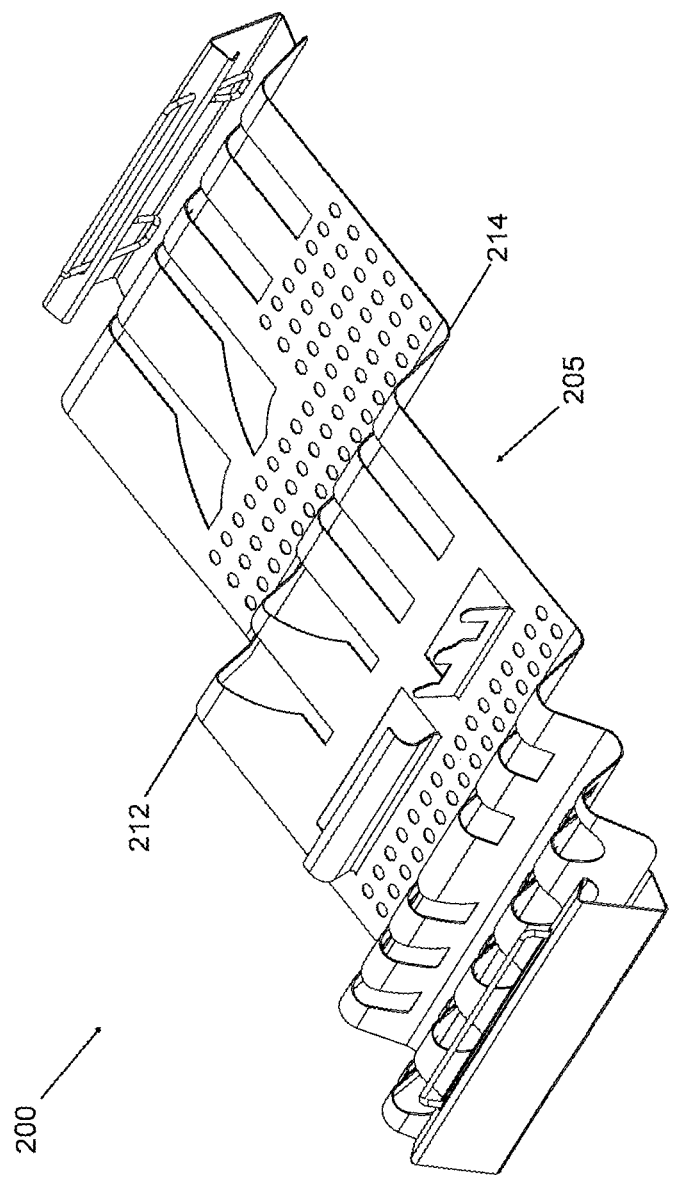
FIG. 2B shows a perspective view of a sterilization tray for instruments, according to an embodiment of the present disclosure.
Figure 2C:
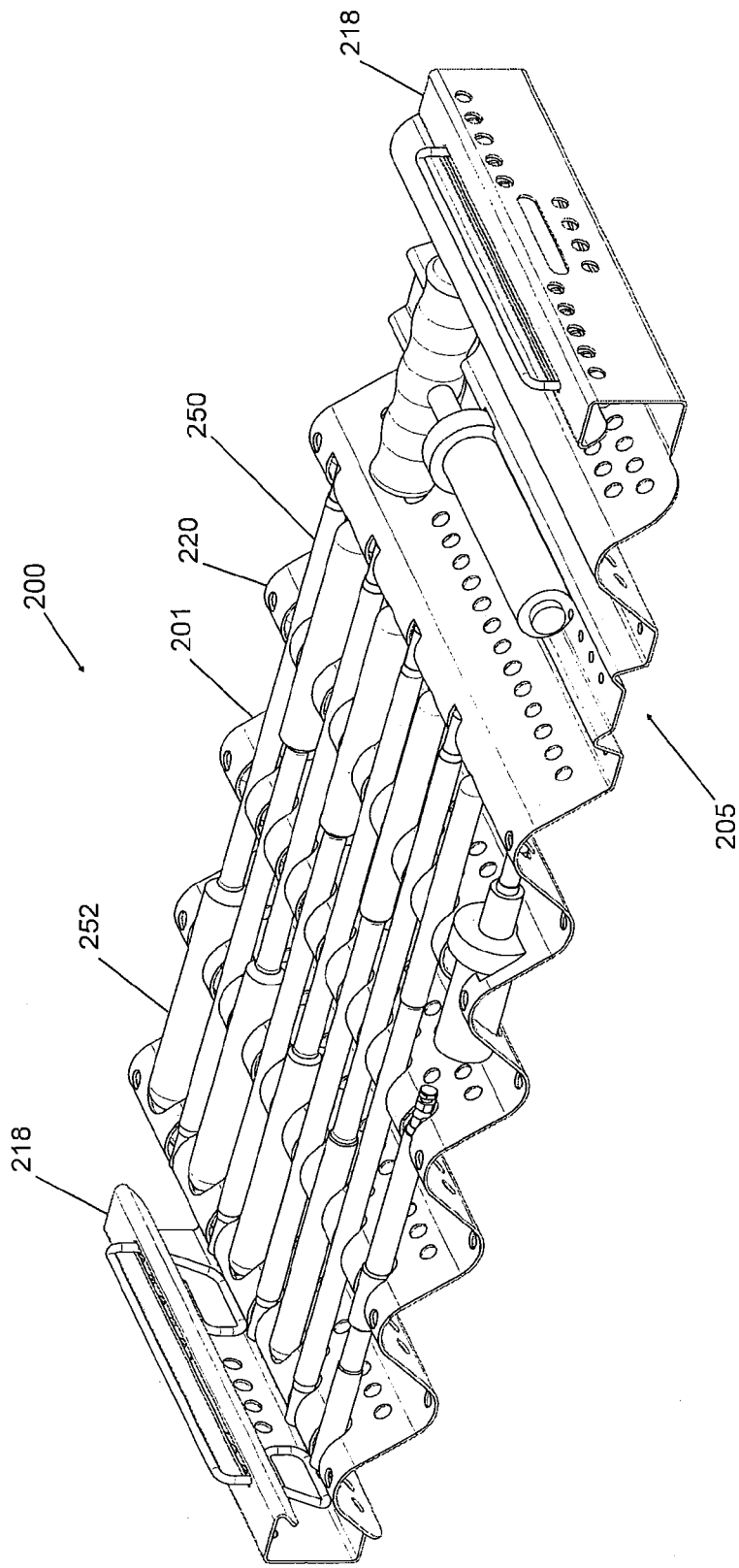
FIG. 2C shows a perspective view of a sterilization tray for instruments including an instrument set, according to an embodiment of the present disclosure.

The wave 105 need not have a uniform sinusoidal profile as shown in FIG. 1C. For example as shown in FIG. 2A, the profile of a center portion 201 of a tray 200 could be comprised of triangular shaped waves 205. Alternatively, the wave 205 could have a substantially saw-tooth shape as shown in FIG. 2B. Alternatively, the wave 205 could have a crescent shape, similar to a shark fin. In short, the wave 205 could assume any suitable profile shape resulting in undulating peaks 212 and troughs 214. Likewise, as shown in FIG. 2A, the overall profile of a center portion 201 may include a combination of different profiles of waves 205 defined by peaks 212 and troughs 214 to accommodate a particular instruments set. Referring to FIG. 2C, some instruments 250 may best be supported for the purposes disclosed herein transversely across the tray 200—that is, parallel to the peaks 212 and troughs 214. In such applications, the center portion 201 may instead include varying cross-sectional profiles as further shown in FIG. 3A. Regardless of the cross-sectional profile of center portion 201, all instruments 250 of an instrument set may be supported such that the topmost edge 252 of each instrument 250 lies on the same plane, the plane lying below a top surface 218, as shown in FIG. 2C. Similarly, though the instruments 250 are depicted lying longitudinally and transversely in the tray 200, one of ordinary skill in the art having the benefit of this disclosure will recognize that the plurality of openings 220 may be formed such that the instruments 250 lie in a plane at any suitable attitude across the peaks 212 and troughs 214 of the tray 200.

In at least one embodiment of the present disclosure, the center portion 101 may further include a plurality of perforations 124 formed through the sheet 110 as shown in FIG. 1B. The perforations 124 may be circular in plan view as shown in FIG. 1B or may be any shape that enables sterilization fluids, such as super-heated steam, liquid sterilants, and oxidizing agents, to pass freely from one side of the sheet 110 to the other. Likewise, the perforations 124 may be arranged in any manner that enables the free flow of sterilization fluids but does not interfere with structure and function of the openings 120.

The sterilization tray 100 may also optionally include at least one, and typically two, handles 130 as shown in FIGS. 1A-1D. A handle 130 may be disposed at each of the first and second ends 102, 103 and may extend through an opening 126 formed in the top surface 118 of each of the first and second ends 102, 103. For example, the handle 130 may extend one-half inch above the top surface 118. As shown in FIG. 1C, the handle 130 may be a bail formed of a wire bent to form at least one retention portion 134 below the top surface 118 and a loop portion 132 for grasping above the top surface 118. During assembly of the handle 130 into the first or second ends 102, 103, the loop portion 132 may be inserted through the opening 126, and the at least one retention portion 134 bent such that the loop portion 132 and the retention portion 134 are not in alignment, thereby trapping the handle 130 within the first or second ends 102, 103.

Figure 4:
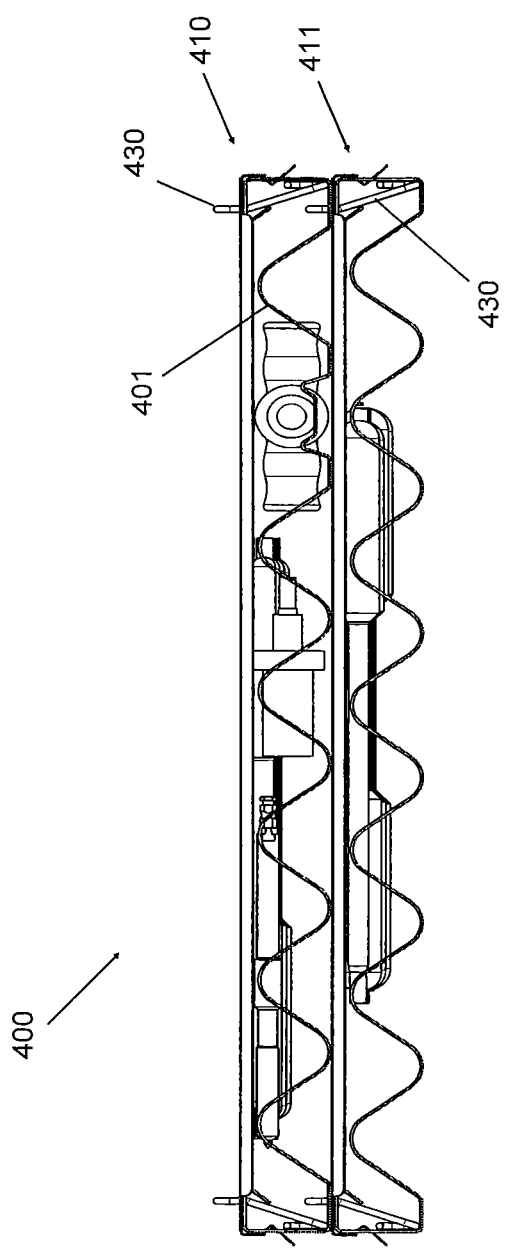
FIG. 4 shows a side view of two sterilization trays for instruments stacked upon one another, including an instrument set in each tray, according to an embodiment of the present disclosure.

In operation, the handle 130 may be lifted by a user until the retention portion 134 contacts the underneath side of the top surface 118. Continuing the lifting motion then lifts the entire tray 100. Upon release, the handle 130 will drop back freely to a resting state due to its own weight. In a resting state, the retention portion 134 of the handle 130 may rest on the center portion 101 such that the loop portion 132 protrudes through the opening 126 in the top surface 118. The protrusion of handle 130 through the opening 126 may provide an indexing feature when multiple trays 100 are stacked one upon another to maintain alignment and at least a partial interlock between trays 100. As shown in FIG. 4, a handle 430 of a lower tray 411 may protrude through a corresponding opening in a center portion 401 of an upper tray 410 and provide positioning and interlocking connectivity between multiple stacked trays, such as upper tray 410 and lower tray 411.

Figure 3A:
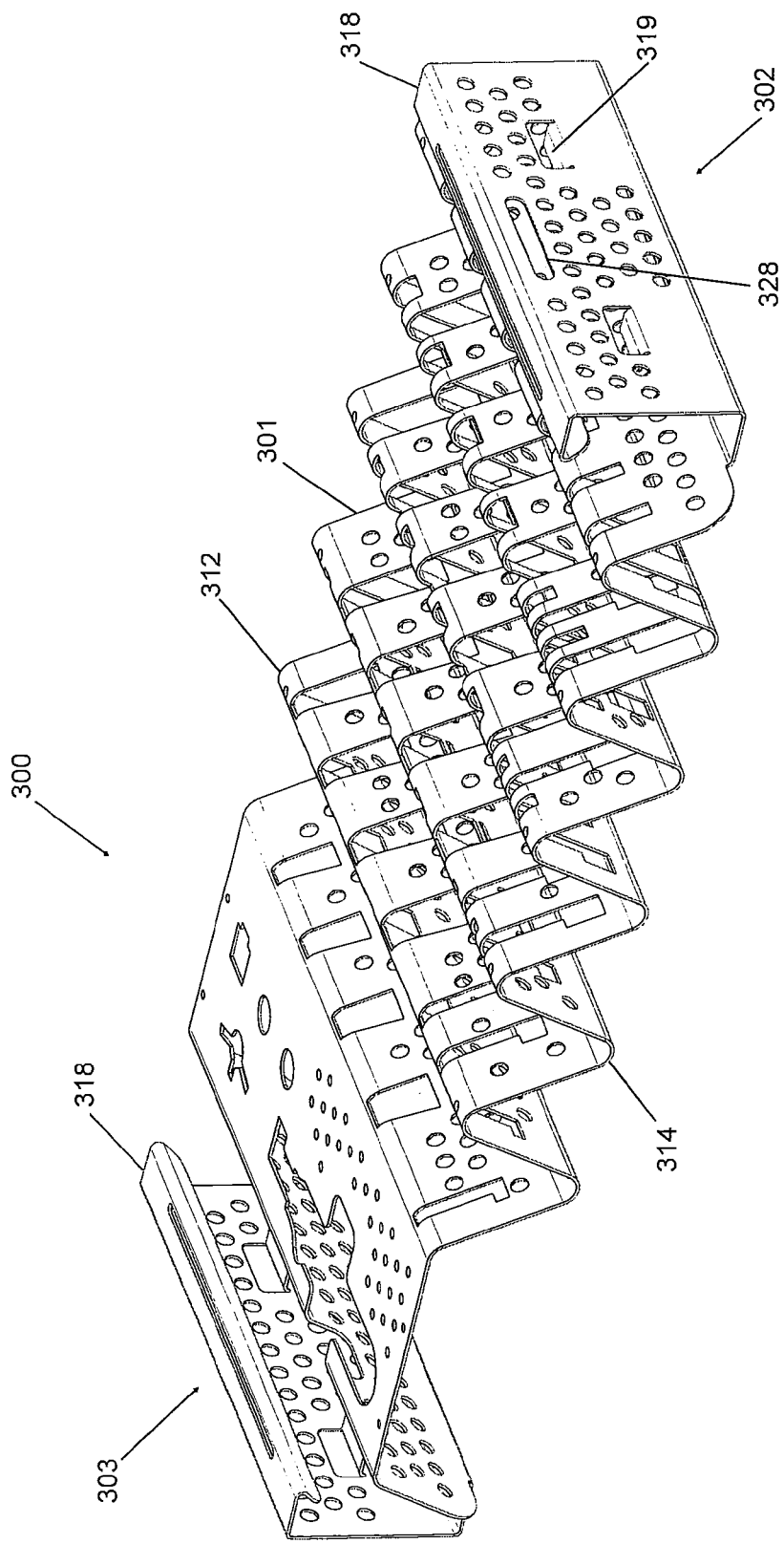
FIG. 3A shows a perspective view of a sterilization tray for instruments, according to an embodiment of the present disclosure.
Figure 3B:
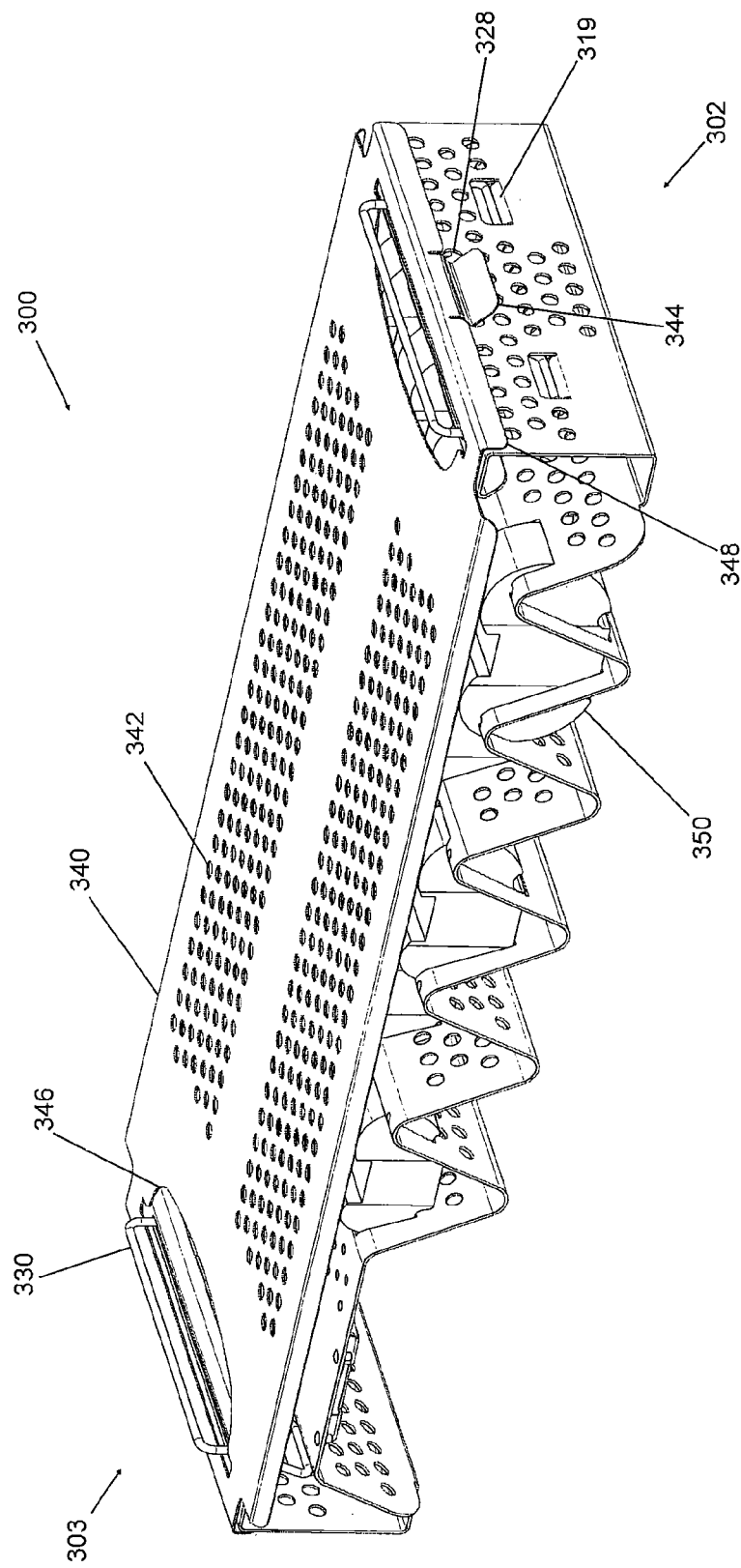
FIG. 3B shows a perspective view of a sterilization tray for instruments including an instrument set and cover, according to an embodiment of the present disclosure.

As noted herein, a tray 300 may be made to accommodate an instrument set including large instruments 350 as shown in FIGS. 3A-3B. The overall height of the tray 300, being the distance between a top surface 318 of a first end 302 (or a second end 303) and a trough 314 of a center portion 301 may be relatively large. In such embodiments, the first and second ends 302, 303 may each include at least one handle tab 319. The handle tab 319 may be formed by cutting and folding a section of the first or second ends 302, 303 toward the center portion 301 such that a handle 330 may contact the handle tab 319 in a resting state, instead of the center portion 301, as shown in FIG. 3B. The location of the handle tab 319 may be selected such that the handle 330 may be identical to the handle 130 (i.e., a handle for a relatively short tray) and yet still protrude the same distance beyond the top surface 318 as the handle 130 extends beyond the top surface 118. Consequently, the same handle component may be used with multiple embodiments of the sterilization tray 100 of varying height.

Various embodiments of the sterilization tray may include a cover. Referring to FIG. 3B for example, the sterilization tray 300 may also include a cover 340. The cover 340 may assist in retaining the instruments 350 in place during transportation, handling, and the sterilization process. The cover 340 may include a plurality of perforations 342 formed through the cover 340. The perforations 342 may be circular in plan view or may be any shape that enables sterilization fluids, such as super-heated steam, liquid sterilants, and oxidizing agents, to pass freely from one side of the cover 340 to the other. Likewise, the perforations 342 may be arranged in any manner that enables the free flow of sterilization fluids but does not interfere with the structure and function of the tray 300. The cover 340 may further include at least one, and typically two, handle openings 346 formed through the cover 340 to enable the handle 330 to protrude beyond the cover 340 and further to enable the handle 330 to provide an indexing feature when multiple trays 300 are stacked one upon another, as described herein.

Figure 5:
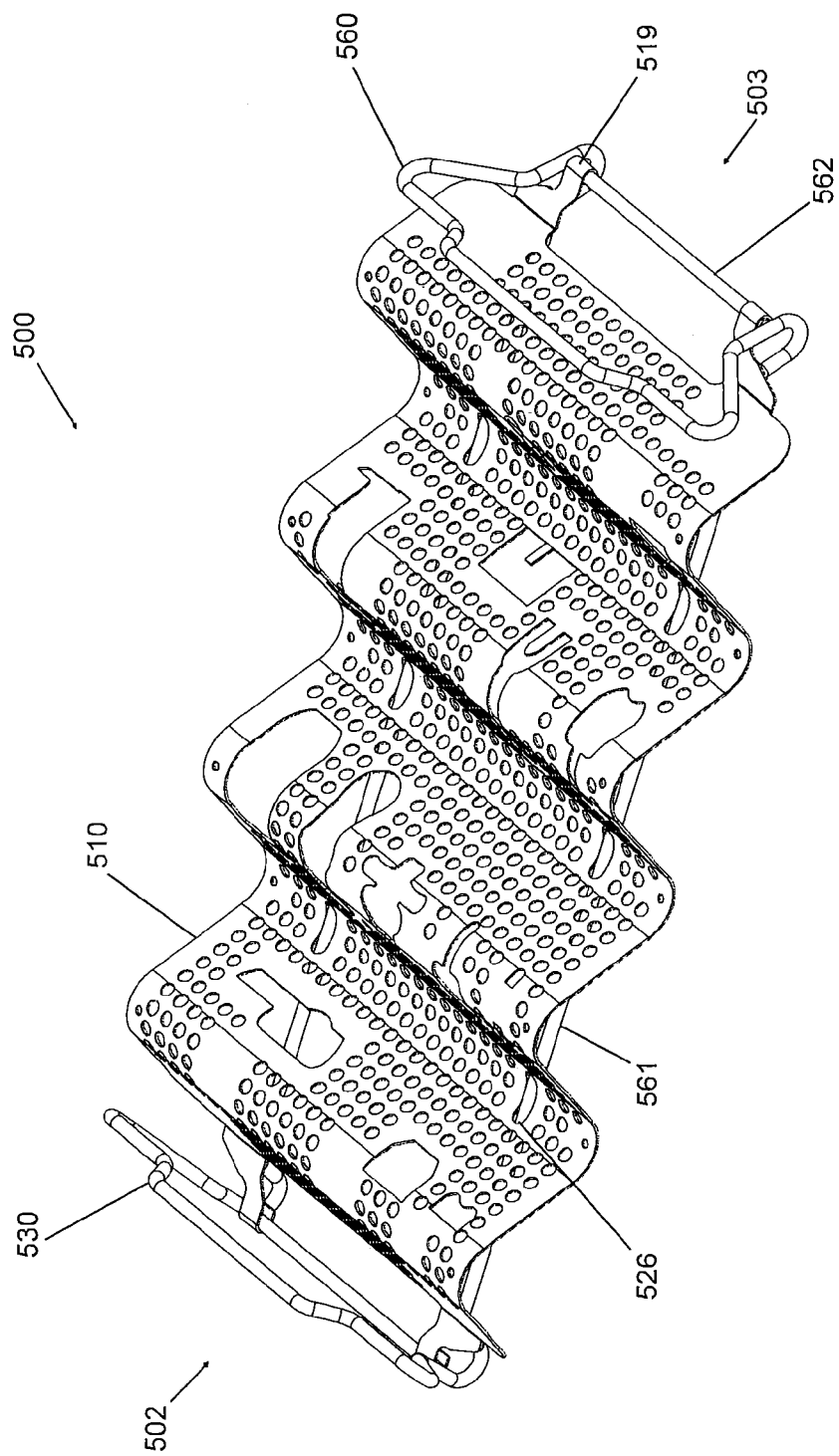
FIG. 5 shows a perspective view of a sterilization tray for instruments with a support frame, according to an embodiment of the present disclosure.

Moreover, the cover 340 may include at least one, and typically two, locking tabs 344 to enable retention of the cover 340 to the tray 300. The locking tab 344 may be formed to engage at least one cover retention opening 328 formed through either or both of the first and/or second ends 302, 303. The locking tab 344 may be formed to act as a leaf spring, such that it is capable of flexing when pulled by a user away from the tray 300, thereby disengaging the cover retention opening 328 and enabling separation of the cover 340 from the tray 300. Furthermore, the cover 340 may include a skirt 348 formed along at least some portion of the periphery of the cover 340 and may have discontinuities at the corners of the cover 430 as shown in FIG. 3B. The skirt 348 may engage the first and second ends 302, 303 to provide indexing of the cover 340 relative to the tray 300. In addition, the skirt 348 may provide structural support to reduce excessive flexing or twisting of the cover 340.

Where a given set of instruments 150 is particularly heavy compared to the flex strength of the sheet 110, a more robust sterilization tray 100 may be required. For example, an instrument set suitable for hip replacement surgery or shoulder surgery may generally be significant heavier than an instrument set appropriate for dental surgery. As shown in FIG. 5, a tray 500 may include a wire support frame 560 to stiffen and strengthen a sheet 510. The support frame 560 may be a single, integrated structure that includes at least one frame member 561 running along the longitudinal length of the tray 500 and may include integral handles 530 formed at frame ends 502, 503. The sheet 510 may include openings 526 formed therethrough, such that the sheet 510 securely engages the support frame 560. The sheet 510 may also include a plurality of end tabs 519 formed to engage the support frame 560 at or near frame ends 502, 503. As shown in FIG. 5, end tabs 519 may wrap around a frame end member 562, thereby securing the sheet 510 to the support frame 560. Further, the sheet 510 may be riveted, welded, or otherwise attached to the support frame 560 at one or more places. The support frame 560 may be formed from sections of bent wire joined together.

Figure 6:
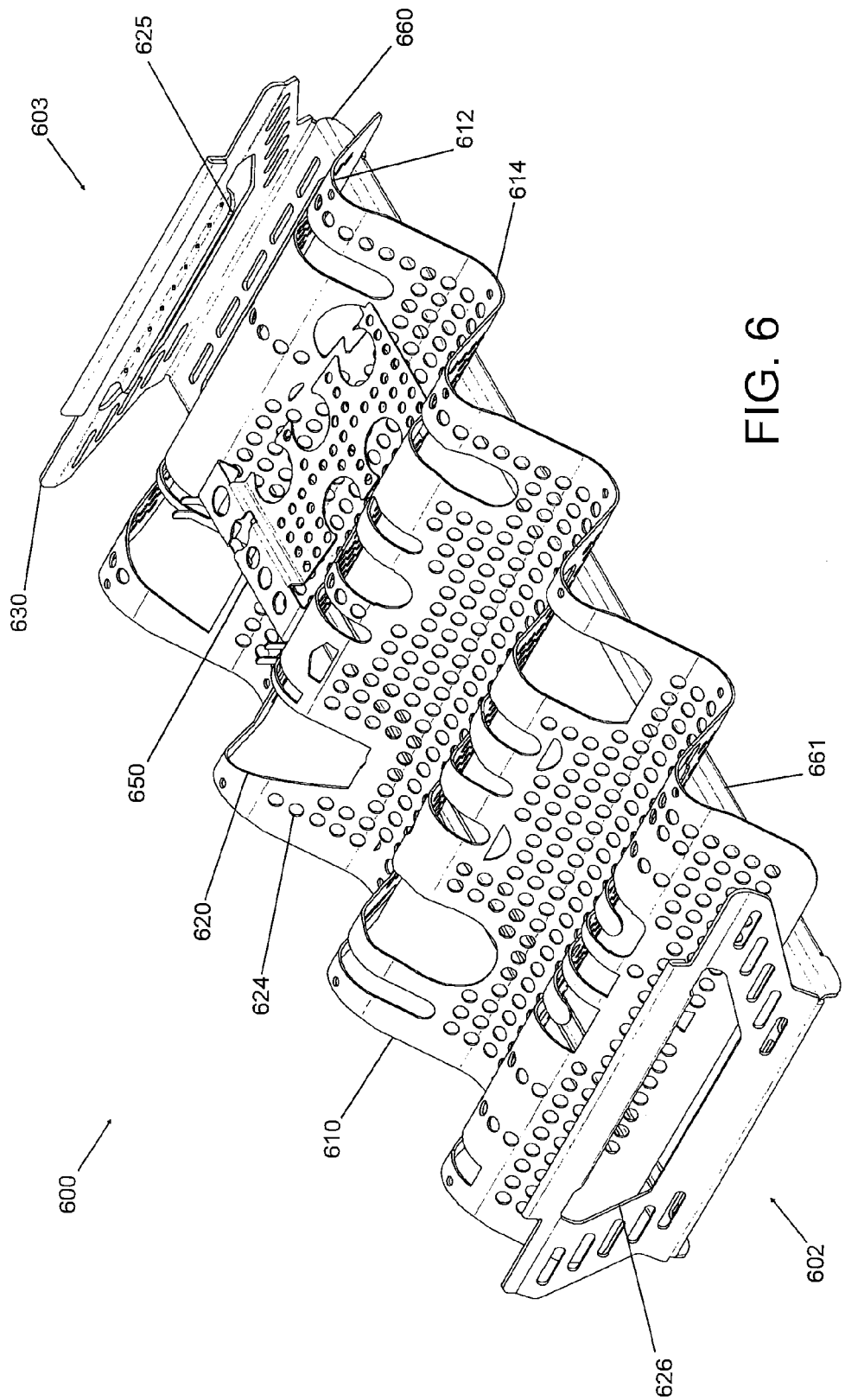
FIG. 6 shows a perspective view of a sterilization tray for instruments with a support frame, according to an embodiment of the present disclosure.

In at least one embodiment according to the present disclosure, a sterilization tray 600 may include a sheet metal support frame 660 to stiffen and strengthen a sheet 610, as shown in FIG. 6. The support frame 660 may be a single, integrated structure that includes at least one frame member 661 running along the longitudinal length of the tray 600 and may further include integral handles 630 formed at frame ends 602, 603. The at least one frame member 661 may be formed with bends and similar features to increase the stiffness of the sheet metal support frame 660. The sheet 610 may be riveted, welded, or otherwise attached to the support frame 660 at one or more places.

Figure 7A:
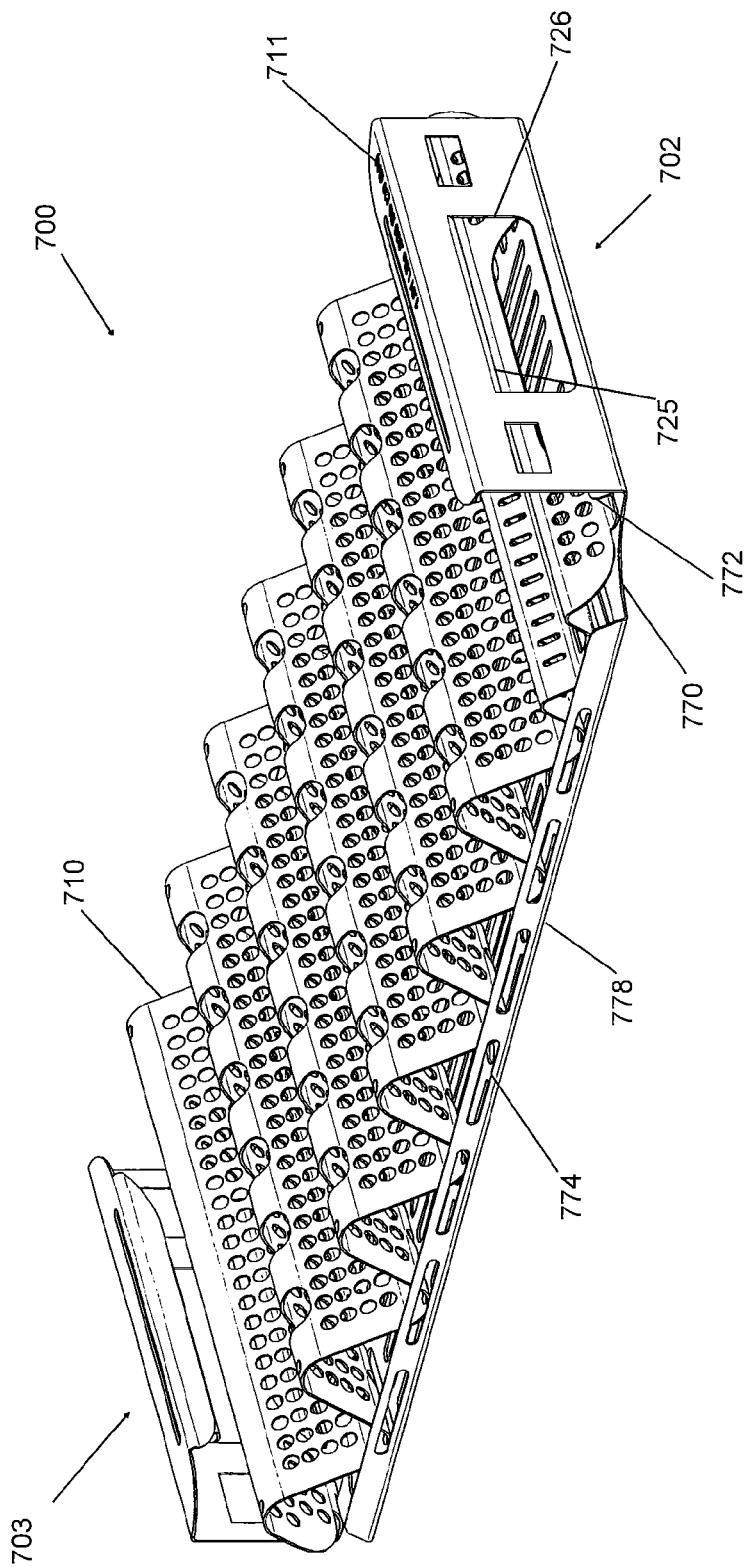
FIG. 7A shows a perspective view of a sterilization tray for instruments with a support panel, according to an embodiment of the present disclosure.
Figure 7B:
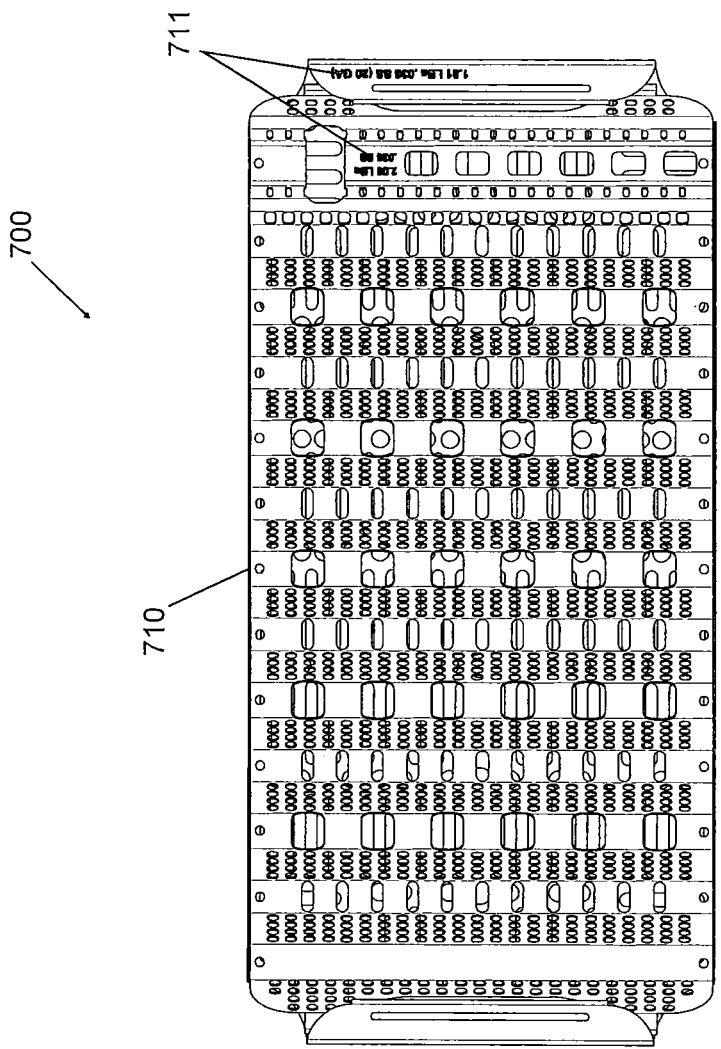
FIG. 7B shows a plan view of a sterilization tray for instruments, according to an embodiment of the present disclosure.

Alternatively, in at least one embodiment, a sterilization tray 700 may include a support panel 770 to stiffen and strengthen a sheet 710 as shown in FIGS. 7A-7B. The support panel 770 may be formed of a single sheet having first and second support ends 702, 703. The support ends 702, 703 may be formed to accept and retain at least one handle 730 (not shown) as disclosed with respect to other embodiments herein. The support panel 770 may also include a skirt 778 formed along at least some portion of the periphery of the support panel 770 to increase its stiffness. The support panel 770 may further include a plurality of openings 774 formed through the support panel 770 that may be of any shape or arrangement that enables the free flow of sterilization fluids but does not interfere with the structure and function of the support panel 770. In addition, the support panel 770 may include at least one locking tab 772 to secure the sheet 710 to the support panel 770 as shown in FIG. 7A. The sheet 710 may be assembled to the support panel 770 by flexing the sheet 710 such that its end edge fits beneath the locking tab 772. The sheet 710 may then be released and, thus, will be trapped and retained between one of the support end portions 702, 703 and the at least one locking tab 772. Alternatively, sheet 710 may be riveted, welded, or otherwise attached to the support panel 770 at one or more places.

In at least one alternative embodiment, one or more handholds 726 may be formed integrally with the first and/or second ends 702, 703 by suitably forming the support panel 770, thereby avoiding a need for the separate handle 730. As shown in FIG. 7A, a handhold 726 may be formed in each of the first and second ends 702, 703 and adequately sized to enable a user to comfortably grasp and lift the tray 700. A comfort feature 725 may be formed in first or second end 702, 703 that includes a curl of material extending inward and upward from the top edge of the handhold 726. The comfort feature 725 may be sized to provide the user with a smooth, rounded edge where the user's hand contacts the tray 700. The sterilization tray 700 may include both one or more handholds 726 and at least one handle 730, enabling a user to lift multiple stacked trays 700, indexed and positioned by the handles 730, using the handholds 726 of the lowermost tray. Likewise, as shown in FIG. 6, the tray 600 may include one or more handholds 626 formed integral with the first and second ends 602, 603 of the sheet metal support frame 660. The one or more handholds 626 similarly may include a comfort feature 625. Similarly, the tray 100 may include one or more handholds 128 formed in the first and/or second ends 102, 103 of the sheet 110.

A sterilization tray of the present disclosure may include indicia imprinted thereon. In at least one exemplary embodiment, as shown in FIG. 7B, the tray 700 may include indicia imprinted on a surface of the sheet 710 and/or the support panel 770. The indicia 711 may include instrument silhouettes, instrument and instrument set identifiers, manufacturer trademarks, and other indicia. The indicia 711 may be imprinted any suitable process.

In at least one embodiment, the sterilization tray 600 may include a bridge 650. The bridge 650 may be a formed sheet adapted to nest within openings 620 and perforations 624 formed in the sheet 610. As shown in FIG. 6, the bridge 650 may span a trough 614 and engage a sheet 610 at or near one or more peaks 612. Accordingly, the bridge 650 may provide additional configurations for supporting and retaining instruments. For example, the bridge 650 may enable the tray 600 to support and retain relatively small instruments where the overall configuration of the tray 600 is formed to be compatible with relative large instruments.

Figure 8A:
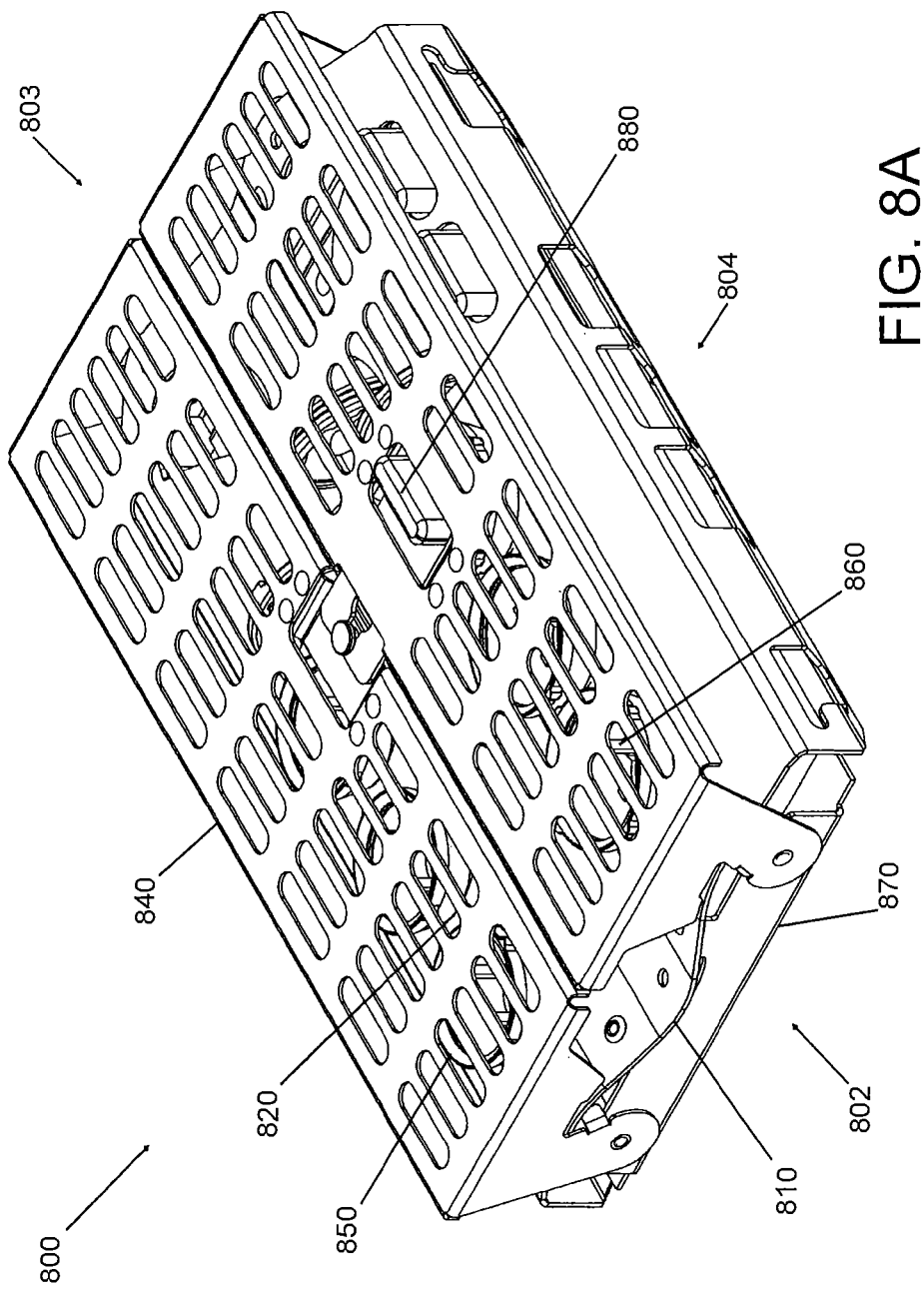
FIG. 8A shows a perspective view of a sterilization tray for instruments with a hinged lid in a closed configuration, according to an embodiment of the present disclosure.

In at least one embodiment according to the present disclosure, a sterilization tray 800 may include a waveform sheet 810 and a hinged lid 840 with a latch 880 operable to lock the lid 840 in a closed configuration as shown in FIG. 8A. The lid 840 is shown in an open configuration in FIG. 8B. The lid 840 may include a first half 841 and a second half 842. The first and second halves 841, 842 of the lid 840 may be hinged to rotate about the sheet 810 between the open and closed configurations. In at least one embodiment, the lid 840 may be hinged to a support panel 870 as shown in FIG. 8A.

Figure 8B:
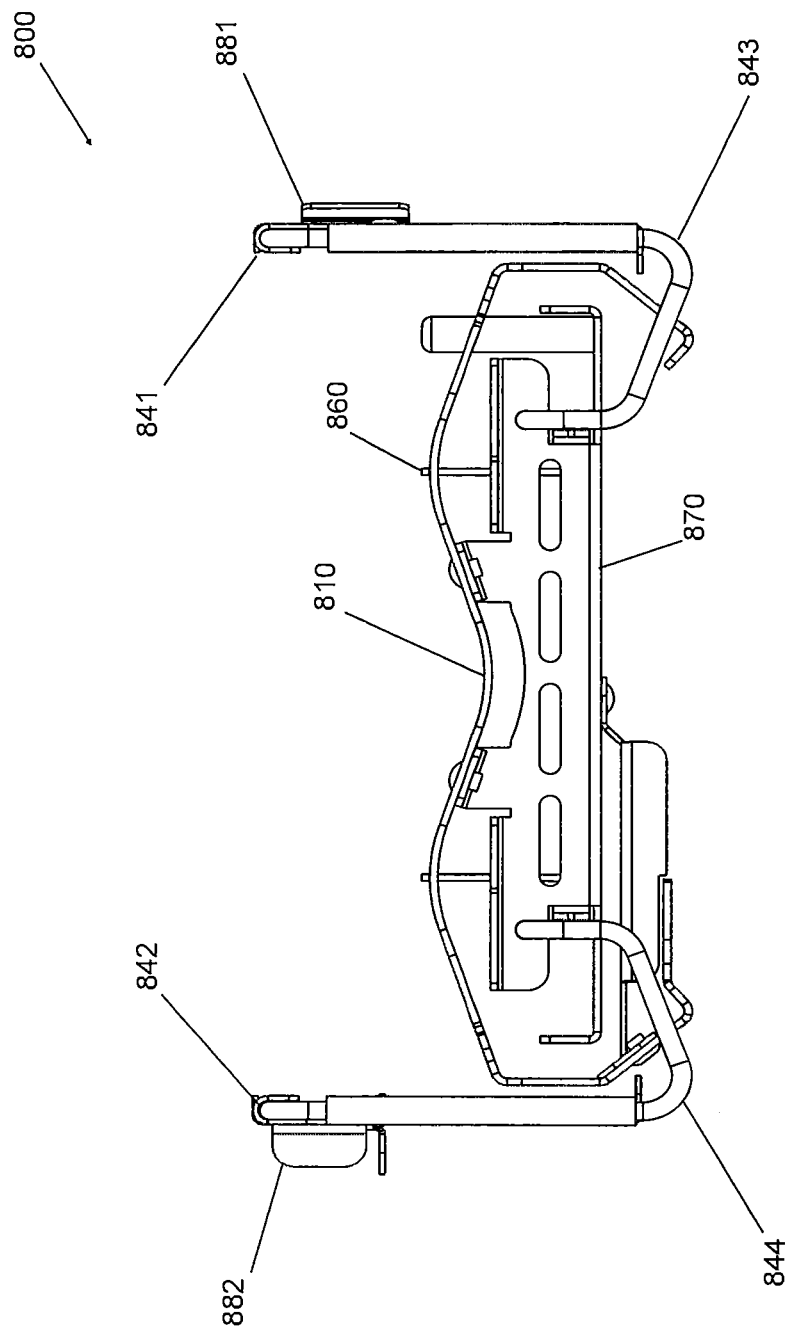
FIG. 8B shows a side view of a sterilization tray for instruments with a hinged lid in an open configuration, according to an embodiment of the present disclosure.

The first half 841 may be a formed sheet as shown in FIG. 8A. Alternatively, the first half 841 may include a lid frame 843 that defines the perimeter of the first half 841 and wraps around the sheet 810 as shown in FIG. 8B, providing structure and support to the first half 841. Likewise, the second half 842 may be a formed sheet as shown in FIG. 8A. Alternatively, the second half 842 may include a lid frame 844 that defines the perimeter of the second half 842 and wraps around the sheet 810 as shown in FIG. 8B, providing structure and support to the second half 842. The first and second halves 841, 842 made by secured together by the latch 880, thus securing the lid 840 in the closed configuration. The latch 880 may include a first latch member 881 and a second latch member 882 mounted to the first and second halves 841, 842, respectively, that engage one another to secure the lid 840 in the closed configuration. Alternatively, the latch 880 may be positioned on a first end 802 or a second end 803 instead of in the middle as shown in FIG. 8A. In an additional embodiment, the lid 841 may include only one half 841 that spans the entire width of the tray 800 and is secured on a side 804 by the latch 880.

The tray 800 may further include one or more posts 860 as shown in FIG. 8A. The one or more posts 860 may extend from the support panel 870 disposed below the sheet 810 toward openings 820 formed through the sheet 810 as shown in FIGS. 8A and 8B. The posts 860 may further extend through the openings 820 as shown in FIG. 8A. The posts 860 enable further positioning and retention of instruments 850 held in the tray 800 and may be formed with a height selected for the specific instrument 850 intended to be retained in a specific opening 820.

Figure 9A:
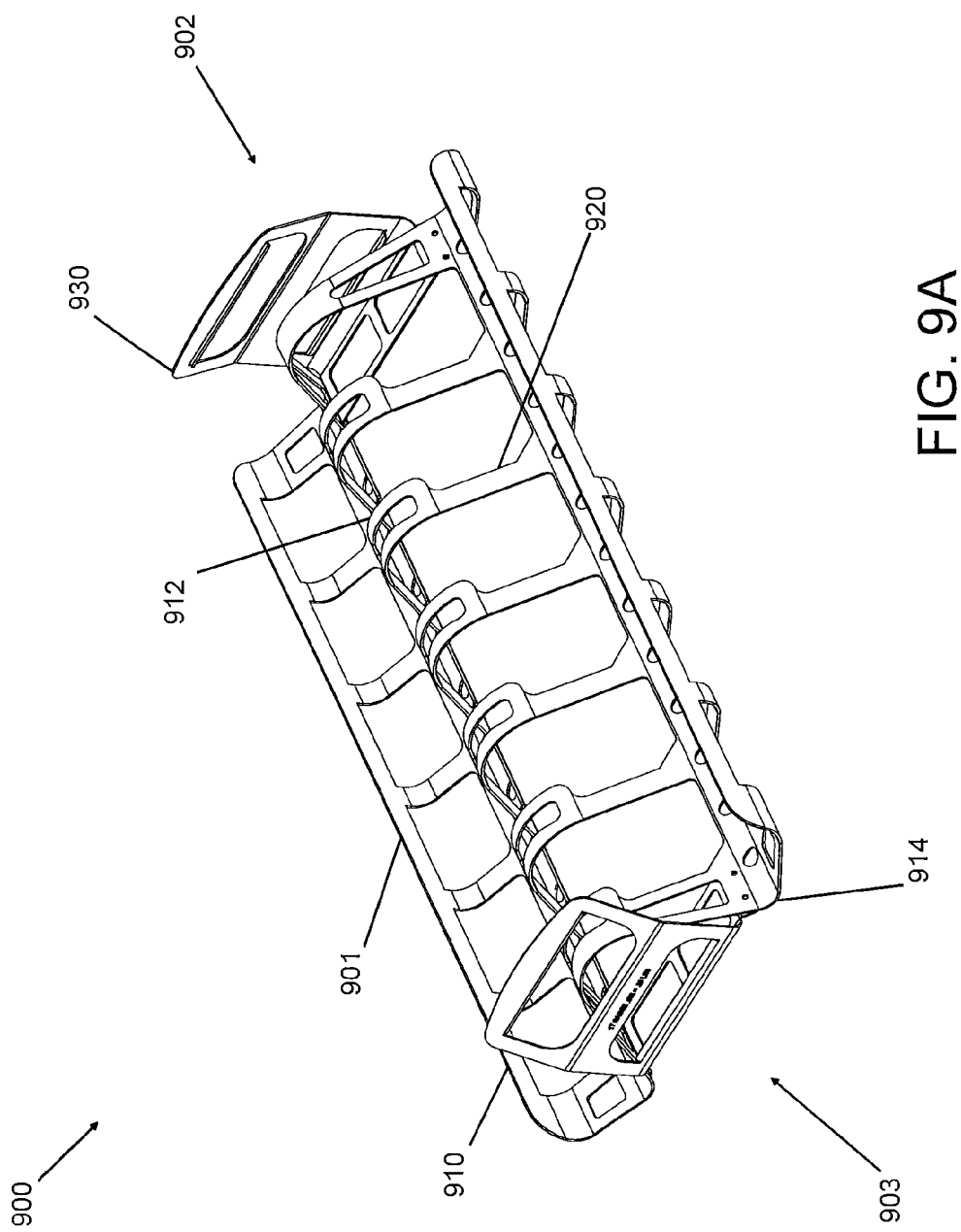
FIG. 9A shows a perspective view of a sterilization rack for instruments, according to an embodiment of the present disclosure.
Figure 9B:
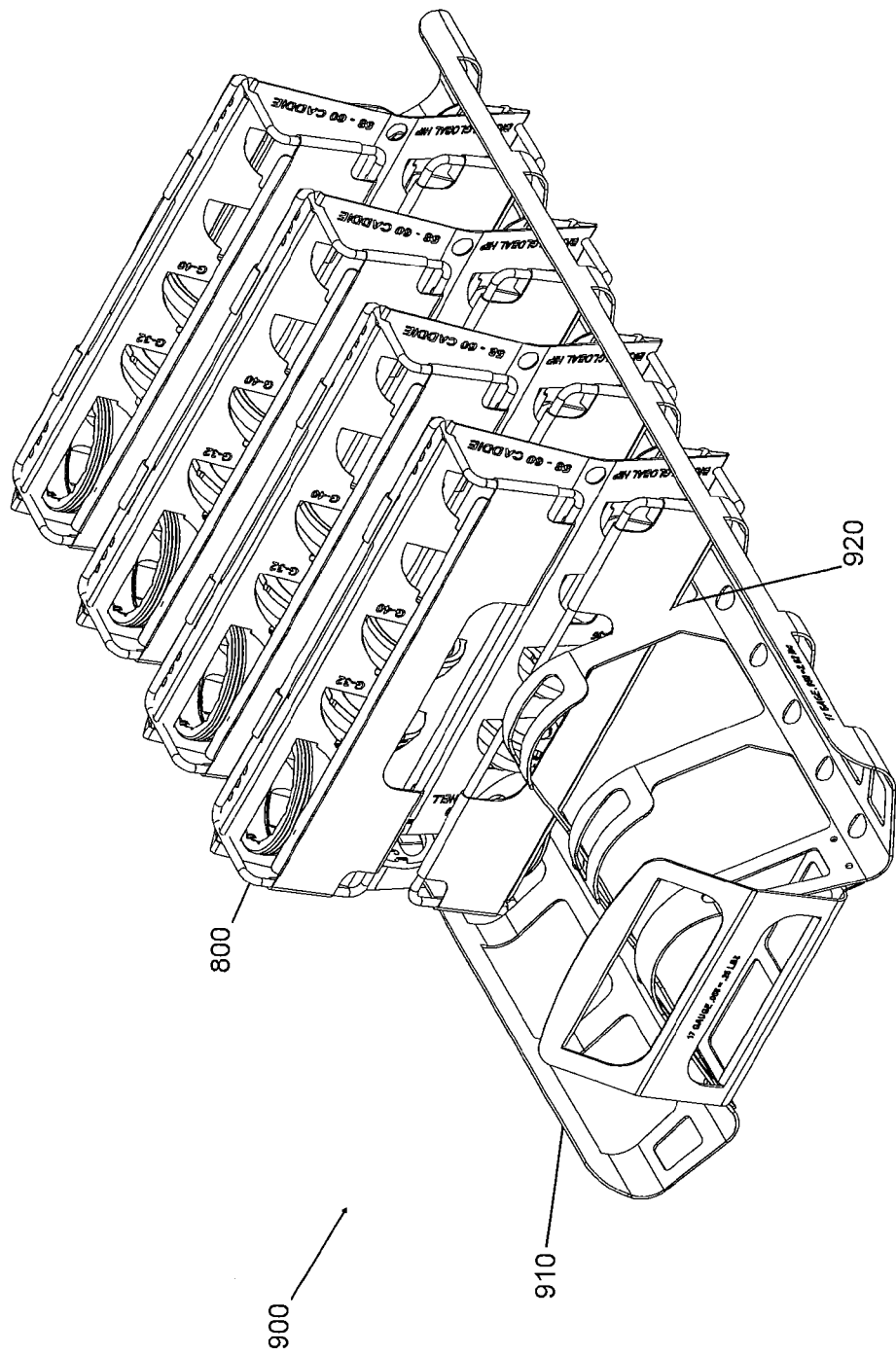
FIG. 9B shows a perspective view of sterilization trays for instruments disposed in a sterilization rack, according to an embodiment of the present disclosure.

A plurality of sterilization trays, such as the tray 800, may be packaged, transported, stored, and sterilized in a sterilization rack 900. As shown in FIG. 9A, the rack 900 may be formed from a sheet 910 having a first end 902, a second end 903, and a center portion 901 therebetween. Similar to other embodiments disclosed herein, the sheet 910 may include an undulating profile having at least one peak 912 and at least two troughs 914. The sheet 910 may further include a plurality of openings 920 formed therethrough and configured to receive and support the tray 800 as shown in FIG. 9B. By varying the size and location of the openings 920, the rack 900 may be configured to receive and support various embodiments of the tray 800. The tray 900 may further include one or more handles 930 formed in the sheet 910. Alternatively, the one or more handles 930 may be formed of separate sheets of material and attached to the formed sheet 910. Accordingly, the rack 900 enables the efficient storage and transportation of multiple sterilization trays 800 in a configuration that further enables the trays 800 to be packaged together in a single sterile package.

The sterilization tray 100, and the various embodiments of the present disclosure, each represent a sterilization tray that is generally lighter in mass, has fewer components, is more easily manufactured and assembled, and is therefore less costly than conventional sterilization trays. Moreover, the undulating peaks and troughs of the sterilization trays according to the present disclosure support and retain the instruments with minimal contact, which improves the efficacy of the sterilization process and reduces the amount of material needed to form the tray. Further, the undulating peaks and troughs increase the rigidity of the tray compared to a flat sheet having openings formed therethrough. As a result, sterilization trays according to the present disclosure may be useful in various fields, and therefore the present disclosure is not limited to the medical applications noted herein.

The tray 100 may be formed in stainless steel, aluminum, or other suitable non-corrosive material of adequate thickness. For example, the tray 100 may be formed in 300-series or 400-series stainless steel having a thickness of 0.036-0.075 inches. The structure of the tray 100 may be formed using a laser cutting or punch press process to form the perforations 124 and all openings 120, 126 and 128, a deburring process to remove all sharp edges, a laser etching process to place instrument silhouettes, identifiers, and other indicia 771 on the surface of the sheet 110, and a press brake process to form the cross-sectional profile of the center portion 101 and the first and second ends 102, 103. The cover 440, sheet metal support frame 660, and support panel 770 may be formed by means similar to the tray 100. Alternatively, the tray 100, handles 130, and cover 440 may be formed in a polymer-based material that is compatible with anticipated sterilization processes, using such polymer processing methods as injection molding, reaction molding and the like.

While various embodiments of a sterilization tray for instruments and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

We claim:

1. A tray for sterilizing and conveying instruments comprising:
   a sheet having a first end, and opposing second end, and a center portion between the first end and second end, wherein the center portion comprises an undulating profile having a plurality of peaks and troughs; and
   a bridge, the bridge comprising a plurality of openings formed therethrough and disposed between adjacent peaks of the sheet, thereby spanning a corresponding trough, wherein the openings are positioned and configured to receive one or more instruments.

2. The tray of claim 1, wherein the center portion comprises a corrugated profile.

3. The tray of claim 1, wherein the center portion comprises a profile selected from the group consisting of: saw-tooth and triangular.

4. The tray of claim 1, wherein the distance between adjacent peaks of the center portion defines a wave having a profile and a length, and wherein the center portion is comprised of one or more waves of non-uniform profile and varying lengths.

5. The tray of claim 1, wherein the first end and second end are each configured at an angle, wherein each end extends beyond the plurality of peaks such that a plurality of trays may be stacked one upon another.

6. The tray of claim 1, the tray further comprising at least one handle.

7. The tray of claim 6, wherein the at least one handle comprises a loop portion extending through a handle opening in the sheet and a retention portion configured to prevent the at least one handle from passing through the handle opening.

8. The tray of claim 6, wherein the at least one handle enables alignment of a plurality of trays stacked one upon another.

9. The tray of claim 6, wherein the at least one handle is formed integral with at least the first end or second end of the sheet.

10. The tray of claim 9, wherein the at least one handle comprises a comfort feature.

11. The tray of claim 1, the tray further comprising a support frame attached to the sheet, the support frame comprising at least one handle.

12. The tray of claim 11, wherein the support frame is comprised of metal wire.

13. The tray of claim 11, wherein the support frame is comprised of sheet metal.

14. The tray of claim 1, the tray further comprising a support panel, the support panel comprising a plurality of openings formed therethrough.

15. The tray of claim 14, wherein the support panel further comprises at least one handle.

16. The tray of claim 14, wherein the support panel further comprises at least one locking tab capable of retaining the sheet to the support panel.

17. The tray of claim 1, wherein the one or more instruments comprise a set of surgical instruments.

18. The tray of claim 1, wherein the sheet comprises a polymeric material compatible with sterilization fluids and sterilization processes.

19. The tray of claim 1, wherein the sheet comprises a non-corrosive metal.

20. The tray of claim 19, wherein the non-corrosive comprises a metal selected from the group consisting of: stainless steel and aluminum.

21. The tray of claim 1, the tray further comprising:
a hinged lid rotatable about the sheet, the lid capable of substantially retaining the one or more instruments; and
a latch capable to be securing the lid in a closed configuration.

22. The tray of claim 21, wherein the hinged lid comprises a first lid member and a second lid member, wherein the latch is configured to secure the first lid member and the second lid member in a closed configuration.

23. The tray of claim 1, the tray further comprising a cover disposed upon and removably attached to the tray, the cover capable of substantially retaining the one or more instruments.

24. The tray of claim 23, wherein the cover comprises a skirt disposed at least partially about a perimeter of the cover and capable of indexing the cover to the sheet.

25. The tray of claim 23, wherein the cover further comprises at least one cover locking tab configured to engage an opening in the sheet and to retain the cover to the sheet.

26. A kit of instruments comprising:
a tray, the tray comprising:
a sheet having a first end, an opposing second end, and a center portion between the first end and second end, wherein the center portion comprises an undulating profile having a plurality of peaks and troughs, and
a bridge, the bridge comprising at least one opening formed therethrough and disposed between adjacent peaks of the sheet, thereby spanning a corresponding trough; and
a set of instruments comprising one or more instruments
wherein the at least one opening is positioned and configured to receive the one or more instruments.

27. The kit of claim 26, the kit further comprising a cover disposed upon and removably attached to the tray, the cover capable of substabtially retaining the set of instruments.

28. The kit of claim 26, the kit further comprising:
a hinged lid rotatable about the sheet, the lid capable of substantially retaining the one or more instruments; and
a latch capable to be securing the lid in a closed configuration.

29. The kit of claim 26, wherein the center portion comprises a corrugated profile.

30. A system for storing instruments, the system comprising:
a rack, the rack comprising:
a rack sheet having a first rack end, an opposing second rack end, and a rack center portion between the first rack end and second rack end, wherein the rack center portion is formed with an undulating profile having at least one peak and at least one trough, and
a plurality of rack openings formed through the rack sheet; and
a kit of instruments, the kit comprising:
a tray, the tray comprising:
a tray sheet having a first tray end, an opposing second tray end, and a center tray portion between the first end and second end, wherein the tray center portion is formed with an undulating profile having a plurality of peaks and troughs, and
a bridge, the bridge comprising at least one opening formed therethrough and disposed between adjacent peaks of the sheet, thereby spanning a corresponding trough,
a set of instruments comprising one or more instruments,
wherein the at least one opening is positioned and configured to receive the one or more instruments,
wherein the rack openings are positioned and configured to receive a plurality of kits.

* * * * *